(12) United States Patent
Antsiferov et al.

(10) Patent No.: US 9,476,841 B1
(45) Date of Patent: Oct. 25, 2016

(54) HIGH-BRIGHTNESS LPP EUV LIGHT SOURCE

(71) Applicant: ISTEQ B.V., Eindhoven (NL)

(72) Inventors: Pavel Stanislavovich Antsiferov, Troitsk (RU); Aleksandr Yurievich Vinokhodov, Troitsk (RU); Vladimir Vitalievich Ivanov, Moscow (RU); Konstantin Nikolaevich Koshelev, Troitsk (RU); Mikhail Sergeyevich Kryvokorytov, Moscow (RU); Vladimir Mikhailovich Krivtsun, Troitsk (RU); Aleksandr Andreevich Lash, Moscow (RU); Vyacheslav Valerievich Medvedev, Troitsk (RU); Yury Viktorovich Sidelnikov, Troitsk (RU); Oleg Feliksovich Yakushev, Korolyev (RU); Denis Alexandrovich Glushkov, Nieuwegein (NL); Samir Ellwi, West Sussex (GB); Pavel Viktorovich Seroglazov, Veldhoven (NL)

(73) Assignee: OOO "Isteq B.V.", Eindhoven (NL)

( * ) Notice: Subject to any disclaimer, the term of this patent is extended or adjusted under 35 U.S.C. 154(b) by 0 days.

(21) Appl. No.: 15/181,509

(22) Filed: Jun. 14, 2016

(51) Int. Cl.
*G01N 21/00* (2006.01)
*G01N 21/956* (2006.01)

(52) U.S. Cl.
CPC ... *G01N 21/956* (2013.01); *G01N 2021/95676* (2013.01)

(58) Field of Classification Search
USPC .............................. 250/493.1, 503.1, 504 R
See application file for complete search history.

(56) References Cited

U.S. PATENT DOCUMENTS 7,525,111 B2 * 4/2009 Bowering .............. B82Y 10/00
250/493.1

* cited by examiner

*Primary Examiner* — Nicole Ippolito
*Assistant Examiner* — Hanway Chang
(74) *Attorney, Agent, or Firm* — Nadya Reingand

(57) ABSTRACT

The invention provides a method and apparatus for a commercially viable EUV light source for EUV metrology and actinic inspection of EUV lithography masks. The invention is carried out using a laser target in the form of a continuous jet of liquid Lithium, circulated in a closed loop system by means of a high temperature pump. The collector mirror is placed outside the vacuum chamber in an environment filled with an inert gas and EUV output to a collector mirror is provided through the spectral purity filter, configured as an EUV exit window for the vacuum chamber. In the vacuum chamber, the input window for the laser beam is coated with a screening optical element. Evaporative cleaning of the EUV spectral purity filter and the screening optical element is provided. The protective shield with a temperature higher than 180° C. may be adjusted around the target jet.

17 Claims, 2 Drawing Sheets

HIGH-BRIGHTNESS LPP EUV LIGHT SOURCE

FIELD OF INVENTION

The invention relates to an apparatus and a method for generating a laser-produced plasma ("LPP"), which provides optical radiation of high brightness in the area of extreme ultraviolet ("EUV"), mainly at 13.5 nm wavelength. Application fields include actinic inspection of lithographic masks and EUV metrology at 13.5 nm.

BACKGROUND OF INVENTION

New generation projection lithography for integration circuits (IC) manufacturing with size of structures below 22 nm is based on usage of EUV radiation near 13.5 nm (13.5+/−0.135 nm), corresponding to reflection band of multilayer Mo/Si-mirrors. Zero defect control of IC is one of the most important metrological processes of modern nanolithography. In the case of mask defect occurrence, defects are projected onto the silicon wafer/substrate which has photoresist hence contributing to the occurrence of micro print defects on the wafer. The common approach in lithography manufacturing is moving away from IC analysis, which is excessively labor and cost intensive at high volume manufacturing, to the analysis of lithographic masks. The EUV lithography mask is a Mo/Si mirror, on top of which a topologic drawing made of material which absorbs radiation at 13.5 nm wavelength is applied. The process of mask inspection is made more effective by means of actinic radiation scanning, i.e. by radiation which has a wavelength equal to the operating wavelength of the lithography process (so called Actinic Inspection). In this case, scanning by EUV with 13.5 nm wavelength makes it possible to detect defects with resolution better than 22 nm.

Zero defect control of lithographic masks during manufacturing and operating is one of the key problems in EUV lithography. Furthermore, production of a light source at 13.5 nm for mask inspection, which has, high brightness and overall high stability, is an area of focus for EUV lithography development. Production of a relatively compact and efficient apparatus is required for the purpose. This apparatus should be on the basis of EUV source with high brightness of radiation equal to $B_{13.5} \geq 30$ W/mm$^2$ sr in wavelength band equal to 13.5+/−0.135 nm and small value of etendue $G=5 \cdot \Omega \leq 10^{-2}$ mm$^2 \cdot$sr, where S-square of source in mm$^2$, $\Omega$-solid angle of EUV output to collector mirror in steradian.

In accordance with one of approaches, known from U.S. Pat. No. 7,307,375, issued on 12 Nov. 2007, high brightness EUV-light source is based on the inductively driven, electrodeless Z-pinch discharge. The EUV source is characterized by simplicity, compactness and relatively low cost. However, Z-pinch is produced in the SiC ceramic bush with orifice diameter 3 mm, which makes it necessary repeated periodic replacement because of significant erosion. Size of radiating plasma is relatively large, and maximal achieved brightness $B_{13.5}$ amounts to ~10 W (mm sr), which is lower than required for a variety of applications, which includes lithographic mask inspection.

The apparatus and method for EUV light generation from laser-produced plasma known from patent application US20150076359, issued on 19 Mar. 2015, don't have this flaw. In the embodiment of invention, the target material is xenon, frozen on the surface of a rotating cylinder, cooled down by liquid nitrogen. EUV radiation of laser-produced plasma is directed to an intermediate focus by the collector mirror, placed in vacuum chamber. The apparatus and method make it possible to achieve a small size of EUV emitting plasma region and high brightness of EUV source without optics contamination.

There are several disadvantages in using this technology: low efficiency of target material, high price of xenon, complicated system of recycling, necessity of high linear speed >15 m/s of cooled cylinder rotating and the related problem of EUV source stability, and lastly, the necessity of collector mirror protection from the effect of heavy ions in Xe-plasma.

The most powerful and high-efficient high-brightness LPP EUV light known, for example, from U.S. Pat. No. 7,897,947, issued on 3 Jan. 2011, contains a nozzle, a laser target, an interaction zone (where the laser hits the target) in a vacuum chamber with gas inlet, an input window for the laser beam, focused at the area of laser action, and an output of the divergent EUV-light beam to the collector mirror, placed in the vacuum chamber. In the method for EUV generation, the form of target droplets is optimized by means of laser pre-pulse and then irradiated by the main laser beam.

Similar systems with usage of tin droplet targets, irradiated by powerful pulse-repetitive $CO_2$ laser made it possible to create most powerful EUV light sources for high-volume manufacturing of IC. However, such EUV sources are rather difficult and expensive due to the use of a complicated laser system with pre-pulse. This complication arises from the laser system along with the need for target droplet synchronization and high speed gas for cooling down and protection of the collector mirror together with its electromagnetic protection system. Periodic replacement of laser targets is used in this apparatus and method instead of a closed cycle of target material. It makes difficult the production of commercially viable EUV sources for inspection and metrology.

Applicability of Lithium (Li) as a target material is declared in U.S. Pat. No. 7,897,947 as one of the most effective target materials besides tin. White using Lithium as a laser target material, the optics are protected from contamination by means of evaporative cleaning. Heating should provide sufficient speed of Li evaporation, i.e. pressure of Li saturated steam at working temperature of optical element should exceed pressure of incoming steam.

In U.S. Pat. No. 7,525,111, issued on 3 Jan. 2011, a window of vacuum chamber with temperature of 350-450° C. is used in the apparatus of EUV generation from laser-produced plasma. However, heating of the window, necessary for its evaporative cleaning, reduces lifetime of sealing gasket and detracts from the apparatus' reliability altogether.

From publication of T. Feig et al. High-Temperature LPP Collector Mirror. Proc. of SPIE Vol. 6151, 61514A, (2006) the collector mirror, working at a temperature up to 500° C. is known. However, a thermal-stress resistant mirror is very expensive. Also, as the mirror is made of pure Mo and Si, these materials begin to react chemically with rising temperatures. The higher the temperature, the faster the reaction, which in turn promotes degeneration of the multi-layer mirror. As a result, evaporative cleaning is a factor which limits the resource of the multi-layer Mo/Si mirror.

SUMMARY OF THE INVENTION

The purpose of the invention is to create a commercially viable EUV light source for EUV metrology and inspection of nano- and microstructures mainly for actinic inspection of EUV lithography masks.

The technical result of the invention is an improvement in reliability and lifetime of the EUV light source, simplification of its construction and lower cost of ownership, while providing high brightness, high spatial and energy stability.

Achievement of the purpose is possible by means of high-brightness laser produced plasma ("LPP") extreme ultraviolet ("EUV") light source comprising a laser target delivered in an interaction zone in vacuum chamber containing a gas inlet, an input window for the laser beam, also comprising a collector mirror.

The apparatus is characterized in that the laser target is a continuous jet of liquid lithium, which is circulated in a closed loop comprising the nozzle and a high temperature pump configured to pump liquid Lithium under clean conditions and to generate the continuous jet of liquid lithium; and the collector mirror is placed outside the vacuum chamber in an environment filled with an inert gas or a mixture of gases under a pressure exceeding pressure inside the vacuum chamber and propagation of EUV-light beam from interaction zone to a collector mirror is provided through the EUV spectral purity filter, configured as an EUV exit window for the vacuum chamber.

In a preferred embodiment of the invention, EUV spectral purity filter is heated up to 350-450° C. and the inner part of spectral purity filter facing the interaction zone is strengthened by a chemically high-resistant material, for example, Molybdenum.

In a preferred embodiment of the invention, at least a part of the continuous lithium jet, placed inside the vacuum chamber, is surrounded by a protective shield with opening for laser beam input and another opening for the EUV light output and the protective shield has temperature more than 180'C.

In a preferred embodiment of the invention, the protective shield is provided with a thermostatic system, which includes a closed loop, filled by a high-temperature heat transfer fluid.

In a preferred embodiment of the invention, a baffle is placed inside the protective shield, and a surface of the baffle, facing the interaction zone, is intended for repulsing the liquid Lithium micro particles mainly in the direction along the liquid Lithium jet.

In a preferred embodiment of the invention, a screening optical element is placed on the laser beam axis between the input window and the interaction zone, the screening optical element is heated up to 350-400° C. and consists of a chemically high-resistant material, with high resistivity to liquid Lithium at high temperatures.

In a preferred embodiment of the invention, the screening optical element is made of sapphire and laser beam light wavelength is in the range of 0.3-3.5 µm.

In a preferred embodiment of the invention, the input window and screening optical element are adjoined to the sub-chamber with gas inlet, providing the pressure difference on both sides of the screening optical element.

In a particular embodiment of the invention, the screening optical element is a focusing lens.

In a preferred embodiment of the invention, the external side of the nozzle has a ceramic lining next to the outlet of the nozzle.

In a preferred embodiment of the invention, etendue of EUV light source output to the collector mirror is in a range of $5 \cdot 10^{-4}$ mm$^2 \cdot$sr to $1.5 \cdot 10^{-2}$ mm$^2 \cdot$sr.

In a preferred embodiment of the invention, the laser beam axis and direction of EUV light output from interaction zone to a collector mirror form two angles to the normal of the lithium jet surface more than 0 degree.

The high temperature pump may be either a magnetohydrodynamic pump ("MHD") or a magnetically driven vane pump with a heatproof magnetic coupling.

In another aspect, the invention, relates to a method for generating extreme ultraviolet ("EUV") light from laser produced plasma ("LPP"), said method comprising: producing a laser target as a continuous liquid Lithium jet, delivered in the interaction zone in a vacuum chamber, while liquid Lithium is pumped on a closed loop system, irradiating at high repetition rate the continuous liquid Lithium jet by a laser beam introduced into the interaction zone through an input window of the vacuum chamber, a screening optical element and an opening in the protective shield, surrounding the continuous liquid Lithium jet, while the optical axis of the laser beam is different from the normal of the continuous liquid Lithium jet surface, and led out EUV light from the laser-produced plasma to collector mirror through another opening in the protective shield and the EUV spectral purity filter, configured as an EUV exit window for the vacuum chamber.

In a preferred embodiment of the invention, a temperature of the protective shield is maintained above lithium's melting point 180° C.

In a preferred embodiment of the invention, a temperatures of the screening optical element and EUV spectral purity filter are maintained in the range of 350 to 450° C.

In a preferred embodiment of the invention, the inert gas pressures on the outward sides of the EUV spectral purity filter and the screening optical element are maintained higher than the pressure inside the vacuum chamber.

DETAILED DESCRIPTION OF PREFERRED EMBODIMENTS

Figure 1:
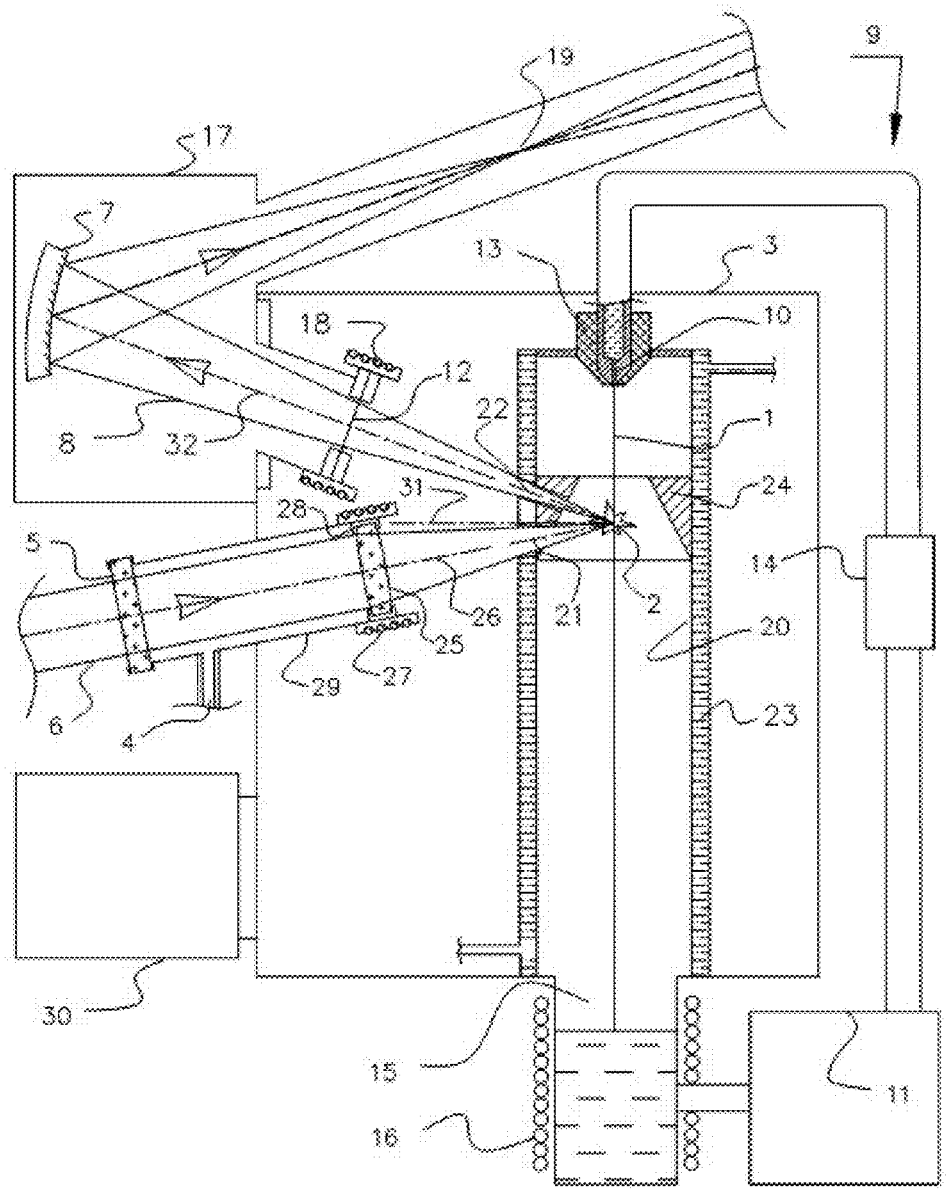
FIG. 1 shows the apparatus and method for EUV light generation from laser-produced plasma, according to the present invention.

According to the preferred embodiment of the invention, illustrated schematically in FIG. 1, a high-brightness LPP EUV light source comprises a laser target 1 delivered in an interaction zone 2 in a vacuum chamber 3 containing a gas inlet 4, an input window 5 for the laser beam 6 (laser beam is focused into interaction zone 2) and also comprises a collector mirror 7, illuminated by divergent EUV-light beam 8 with apex in interaction zone 2.

The laser target 1 is a continuous jet of liquid lithium, which is circulated in a closed loop system 9 comprising the nozzle 10 and a high temperature pump 11, configured to pump liquid Lithium under clean conditions and to generate the continuous jet of liquid lithium.

The collector mirror 7 is placed outside the vacuum chamber 3 in an environment filled with an inert gas or a mixture of gases under a pressure exceeding the pressure inside the vacuum chamber 3.

Propagation of EUV-light beam 8 from interaction zone 2 to a collector mirror 7 is provided through the EUV spectral purity filter 12, configured as an EUV exit window for the vacuum chamber 3.

High-brightness LPP EUV light source implemented in accordance with the present invention has a number of advantages. Advantages related to the use of lithium as the plasma fuel are as follows:

high conversion efficiency, close to the maximum achieved for various types of plasma fuels, of Li EUV source;

relatively low lithium melting point of 180.54° C., simplifying formation of liquid metal laser target;

low specific weight of Li, simplifying its circulation through the interaction zone with a high velocity, necessary for EUV source operation at a high repetition rate;

high efficiency of evaporative removal of deposited lithium by heating of optical elements to around 400° C.;

small atomic weight of Li ions, causing less erosion of optical elements, which lengthens the lifetime of the optics;

high spectral purity of Li EUV source, providing decrease of radiation load on EUV optics and increase of its lifetime.

The circulation of liquid Lithium in a closed loop system 9 with a high temperature pump 11 provides almost unlimited time of continuous operation of EUV source at low operating cost.

In one embodiment of the present invention, a high temperature pump 11, configured to pump liquid Lithium under clean conditions and to generate the continuous jet 1 of liquid lithium, is a MHD pump.

In preferred embodiment of the present invention, high temperature pump 11 is a vane type pump with heatproof magnetic coupling. Its detailed description is given in patent RU2488716, issued on 27 Jul. 2013 and in patent application WO2013/157986.

While using above listed types of pumps, target material is not affected by outer atmosphere. It provides both purity of chemically-active Lithium and high efficiency of EUV light, source during long-term operation.

Unlike LPP EUV-light sources with a jet of droplet targets, usage of continuous liquid metal jet as laser target provides high spatial and energy stability of EUV source and rather simplifies the apparatus and lowers its cost. In particular, the nozzle 10 is simplified as far as it's not necessary to combine it with piezo-electrical mechanism for breaking jet into droplets.

In preferred embodiment of the invention, external side of the nozzle 10 has a ceramic lining 13 next to the outlet of the nozzle, in order to prevent its moistening and to provide high stable jet target.

The closed loop system 9 is supplied with filter elements 14 for cleaning of liquid Lithium and preventing blockage of the nozzle 10; preferably, these filter elements have decreasing size of pores from 100 to 5-10 μm along the Lithium flow. The closed loop system 9 can be completed with a freeze trap to increase effectiveness of cleaning and operating time of the filter elements 14. Cleaning process consists of cooling liquid Lithium down to temperatures close to melting temperatures, with composition of oversaturated solution and activation of the process of solution crystallization, followed by disposal of precipitated crystals from metal flow. The trap can be combined with a jet receiver 15. Jet receiver 15 may be a part of the closed loop system 9 and a part of the vacuum chamber 3. The jet receiver 15 is preferably completed with a thermostatic system, designed to maintain Lithium temperature inside it at the given level, exceeding the melting temperature. The thermostatic system of the jet receiver 15 can contain ohmic heater 16 and heat insulating cover. Other components of the closed loop system 9 may also be completed with heat insulating, covers and ohmic heaters necessary for start launching.

All details and joints of the closed loop system 9, which are in contact with liquid Lithium, are made of materials resistant to liquid Lithium atmosphere, or have coatings resistant to liquid Lithium atmosphere.

Placement of the collector mirror 7 outside the vacuum chamber 3, for example, in a clean optical box 17 in the environment of gas or a mixture of gases under a pressure exceeding pressure inside the vacuum chamber allows gas to flow through the slit gap around the perimeter of the EUV spectral purity filter 12 thus preventing the entering of lithium vapor to the collector mirror 7 and to the outer side of the EUV filter 12.

In preferred embodiments of the invention, the EUV spectral purity filter 12 is heated up to 350-450° C. and the inner part of the spectral purity filter facing the interaction zone 2 is strengthened by a chemically high-resistant material, for example, Molybdenum.

The spectral purity filter, preferably including foil, e.g. zirconia (Zr), with a relatively high transparency at wavelength 13.5 nm, can be applied on a high-transparent supporting grid.

Evaporation cleaning is provided by a system of ohmic or induction heating 18, accomplished with the possibility of temperature stabilization of the EUV spectral purity filter 12 at a level of 350-450° C. These temperatures are high enough to achieve Lithium evaporation at a speed higher than its inflow.

The collector mirror 7 is an ellipsoid mirror of grazing incidence, or, according to FIG. 1, a multilayer Mo/Si mirror with an angle of incidence close, to normal. A divergent EUV-light beam 8, with apex in primary focus of the collector mirror 7, combined with the interaction zone 2, is redirected to a second focus point or to an intermediate focus 19 by the collector mirror 7. An intermediate focus 19 forms an interface between the EUV light source and EUV projection tool; it is not shown in FIG. 1 for simplicity. According to the invention, the EUV spectral purity filter 12 serves to protect the collector mirror from Lithium contamination and to provide spectral purity of clean EUV light, shutting off laser radiation scattered by the target and out of band EUV In preferred embodiments of the invention, the etendue of EUV light source output to the collector mirror 7 is in a range of $5 \cdot 10^{-4}$ mm$^2 \cdot$sr to $1,5 \cdot 10^{-2}$ mm$^2 \cdot$sr, that meets the requirements of EUV sources for actinic inspection. In such cases, taking into account the fact, that the square of EUV emitting region of laser-produced plasma is $\sim 10^{-2}$ mm$^2$, and the distance to the collector mirror is less than 0.5 m, characteristic dimensions of the collector mirror 7 and of EUV spectral purity filter 12 do not exceed few tens of millimeters. This simplifies the apparatus and makes it cost effective.

In preferred embodiments of the invention, at least a part of the continuous lithium jet 1, placed inside the vacuum chamber 3, is surrounded by a protective shield 20 with opening 21 for laser beam 6 input and another opening 22 for the EUV light output to collector mirror 7. Here the EUV light output is represented by EUV-light beam 8 illuminating the collector mirror 7. The protective shield 20 has a temperature more than 180° C. that prevents Lithium accumulation on its walls.

The use of the protective shield 20, which has only small openings 21, 22 for focused laser beam input and EUV light output, makes it possible to effectively suppress the leakage of Lithium outside of the closed loop system 9. This provides long lifetime of the apparatus and lower cost of ownership.

In preferred embodiments of the invention, to ensure heat removal from the interaction zone 2, the protective shield 20 is provided with a thermostatic system, which includes a closed loop, filled with a high-temperature heat transfer fluid 23.

The thermostatic system may contain a heat-exchanger and circulator pump for hot fluids. Circulation of high-temperature heat transfer fluid 23 can be carried out through a channel or channels of the protective shield 20.

In preferred embodiments of the invention, baffle 24 is placed inside the protective shield 20 and a surface of the baffle, facing the interaction zone 2, is intended for repulsing the liquid Lithium micro particles mainly in the direction along the liquid Lithium jet 1. Baffle 24 provides the suppression of leakage of liquid Lithium micro particles through openings 21 and 22 of the protective shield 20. For accomplishment of this function, the surface of baffle 24, facing the interaction zone, has a slant towards the jet 1 different from the slant of the protective shield 20. For example, the baffle 24 surface, facing the interaction zone, can be conic. Another function of the baffle is to prevent the protective shield's internal surface from impacts of corpuscular and light radiation from the interaction zone.

In preferred embodiments of the invention, a screening optical element 25 is placed on the laser beam axis 26 between the input, window 5 and the interaction zone 2, the screening optical element 25 is heated up to 350-400'C and consists of a chemically high-resistant material, with high resistivity to liquid Lithium at high temperatures.

The ohmic or induction heating system 27 of the screening optical element 25 is designed with the capability to maintain temperature at a predetermined level. The heating of the screening optical element 25 may be through its mount 28.

In preferred embodiments of the invention, the screening optical element 25 is made of sapphire and the laser beam light wavelength is in the range of 03-3.5 um.

Manufacturing of the screening optical element 25 using sapphire or synthetic sapphire means it can operate under the extreme conditions of high temperatures, mechanical loads, corrosion environment and radiation, hence its, long life time. Together with that it is possible to use different types of lasers (with a variety of wavelengths) which are in the range of sapphire optical transparency of 0.3-3.5 μm, such as compact and reliable high-efficient, high-repetition rate Nd:YAG lasers.

In preferred embodiments of the invention, the input window 5 and screening optical element 25 are adjoined to the sub-chamber 29 with gas inlet 4, providing the pressure difference on both sides of the screening optical element 25.

The system of oil-free vacuum pumping 30 in the vacuum chamber 3 is located outside the sub-chamber 29. It provides differential pressure of gas on both sides of the screening optical element 25. As a result, there is a gas leakage through the slit gap on the perimeter of the screening optical element 25, which prevents Lithium vapor deposition on input window 5 and on the external side of the screening optical element 25. At least, a part of the sub-chamber 29, adjoining the screening optical element 25, can be made for example of thin stainless, steel, with low thermal conductivity for thermal insulation of the vacuum chamber 3 and the screening optical element 25 with temperature of about 400° C. In this embodiment of the invention, an input window 5 is reliably protected against contamination without heating, which increases the reliability of the input window sealing and lifetime of the sealing gasket of the input window.

In embodiment of the invention, the screening optical element 25 is a focusing lens, FIG. 1. It makes it possible to minimize focal distance and to decrease laser beam focal spot size. As a result, brightness of EUV light source increases.

In embodiment of the invention, the focusing lens may be installed outside the input window 5. In particular embodiment of the invention, the input window 5 may be a focusing lens.

Primary motion of plasma and particles of liquid Lithium from the interaction zone 2 is on a normal line 31 to the jet 1 surface. In this connection, in preferred embodiment of the invention the laser beam axis 26 and the direction 32 of EUV light output from the interaction zone to a collector mirror form two angles to the normal 31 of the lithium jet 1 surface more than 0 degree. This improves protection of both screening optical element 25 and EUV spectral purity filter 12 against contamination.

On the other hand, maximum brightness is achieved towards the normal of the lithium jet and coincides with the direction of the primary plasma and debris motion. With an increase in angle the debris will be lower but the brightness will also be lower. Thus the angle between EUV beam axis 32 and normal 31 of the lithium jet should not be large, not more than 30 degree.

Figure 2:
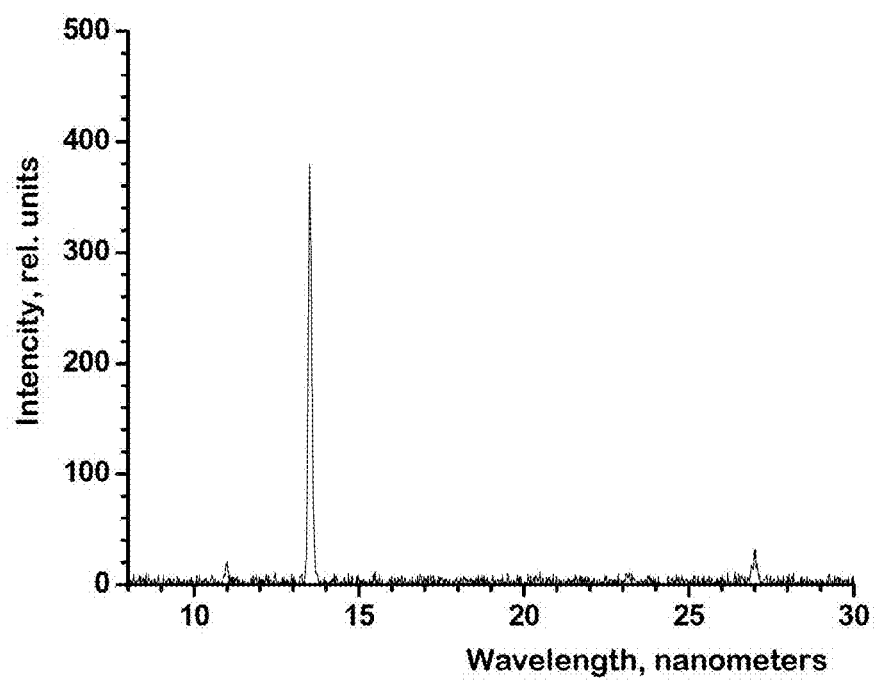
FIG. 2 shows spectrum of EUV light, produced in accordance to present invention.

FIG. 2 shows EUV spectrum for embodiment of the invention with usage of a solid-state Nd:YAG laser with wavelength of 1064 nm, pulse duration 17 ns and power density on the target of $1.1 \cdot 10^{11}$ W/cm$^2$. Laser wavelength corresponds to the range of optical transparency of sapphire, applied as a material of the screening optical element 25. As seen from FIG. 2, the high spectral purity of EUV emission from Li-plasma is provided under these parameters. Planned parameters of the LPP EUV source, worked out in accordance with this invention, are:

Lithium jet speed—up to 20 m/s
jet diameter—1 mm
distance from interaction zone to nozzle—50 mm
distance from interaction zone to EUV window—150 mm
EUV window diameter—20 mm
transparency of EUV window—40-50%
conversion efficiency, $CE_{13,5}$—up to 2.5%
spatial angle of EUV output—$\Omega$=0.012 sr
EUV output energy, $B_{13,5}$—6 μJ/pulse
EUV average output power, $P_{13,5}$—60 mW
brightness of EUV source, $B_{13,5}$—up to 1 kW/mm$^2$ sr.

Method for generating extreme ultraviolet light from laser produced plasma is implemented in the following way.

The vacuum chamber 3 is evacuated by an oil-free vacuum pumping system to pressure less than $10^{-8}$ mbar, removing fragments of gaseous components, such as nitrogen and carbon, which react with Lithium. Then by means of gas leak valves neutral gas is fed through gas inlets 4 to the clean optical box 17 with the collector mirror 7 and to the sub-chamber 29 with the input window 5 and the screening optical element 25.

A laser target is produced as a continuous liquid Lithium jet 1, delivered in the interaction zone 2 in a vacuum chamber 3, while liquid Lithium is pumped on a closed loop system 9. Circulation of liquid Lithium under clean conditions in the closed loop system 9 is provided by means of a pump 11 in the form of an MHD-pump or vane-type pump with heatproof magnetic coupling.

Continuous liquid Lithium jet 1 is irradiated at high pulse repetition rate by a laser beam 6, introduced into the interaction zone 2 through an input window 5 of vacuum chamber 3, a screening optical element 25 and an opening 21 in the protective shield 20, surrounding the continuous liquid Lithium jet, while the optical axis 26 of laser beam is different from the normal 31 of the continuous liquid Lithium jet surface.

EUV-light beam 8 is led out from the laser-produced plasma to collector mirror 7 through another opening 22 in the protective shield 20 and the EUV spectral purity filter 12, configured as an EUV exit window for the vacuum chamber 3.

During operation, the temperature of the protective shield 20 is maintained at a level higher than Lithium's melting temperature 180° C., avoiding the Lithium accumulation on its walls. The protective shield 20 prevents the leakage of the laser target material outside the closed loop system 9 and ensures heat management for the interaction zone.

By means of the heating system 18, 27 the temperatures of the screening optical element 25 and EUV spectral purity filter 12 are maintained in the range of 350 to 450° C., providing their evaporative cleaning.

Furthermore, the inert gas pressures on the outward sides of the EUV spectral purity filter 12 and the screening optical element 25 are maintained higher than the pressure inside the vacuum chamber 3, thus preventing the entering of lithium vapor to the collector mirror 7 and to the input window 5.

The apparatus and method for EUV light generation from laser-produced plasma, made according to the present invention, have the following main advantages:

Continuous operation of the apparatus is provided with almost limitless use of resources, therefore removing the need to open the vacuum chamber to replace the Li target, unlike the tin droplet target approach.

High spatial and energy stability of EUV-light source is provided.

Usage of Li as the target material decreases degradation of optical elements under the influence of corpuscular radiation compared to the usage of tin.

Relative simplicity of evaporative cleaning is achieved for optical elements.

Long operating time of the collector mirror is achieved by locating it outside the vacuum chamber.

Unlike tin and xenon plasma, high spectral purity of Li LPP EUV source decreases radiation load on the collector mirror and EUV spectral purity filter, providing increase in their lifetime.

Long lifetime of input window for the laser beam is achieved by usage of a screening optical element with gas protection.

Simple design of EUV source, increase in ease of operation and lower cost of ownership are achieved.

INDUSTRIAL APPLICATIONS

The proposed apparatus and method are intended for EUV metrology, inspection of nano- and microstructures including actinic inspection of EUV lithography masks.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The invention claimed is:

1. A high-brightness laser produced plasma ("LPP") extreme ultraviolet ("EUV") light source, comprising: a laser target (1) delivered in an interaction zone (2) in a vacuum chamber (3) containing a gas inlet (4), an input window (5) for a laser beam (6); also comprising a collector mirror (7), characterized in that the laser target is a continuous jet of liquid Lithium (1), which is circulated in a closed loop system (9) comprising a nozzle (10) and a high temperature pump (11), configured to pump liquid Lithium under clean conditions and to generate the continuous jet of liquid lithium;

the collector mirror (7) is placed outside the vacuum chamber in an environment filled with an inert gas or a mixture of gases under a pressure exceeding pressure inside the vacuum chamber and an output of EUV-light beam (8) from an interaction zone (2) to the collector mirror (7) is provided through an EUV spectral purity filter (12), configured as an EUV exit window for the vacuum chamber.

2. The apparatus according to claim 1, wherein the EUV spectral purity filter (12) is heated up to 350-450° C. and an inner part of the spectral purity filter facing the interaction zone is strengthened by a chemically high-resistant material.

3. The apparatus according to claim 1, wherein at least a part of the continuous lithium jet (1), placed inside the vacuum chamber (3), is surrounded by a protective shield (20) with an opening (21) for laser beam input and another opening (22) for the EUV light output and the protective shield (20) has temperature more than 180° C.

4. The apparatus according to claim 3, wherein the protective shield (20) is, provided with a thermostatic system, which includes a closed loop, filled by a high-temperature heat transfer fluid (23).

5. The apparatus according to claim 3, wherein a baffle (24) is placed inside the protective shield (20) and a surface of the baffle, facing the interaction zone, is intended for repulsing the liquid lithium micro particles mainly in a direction along the liquid Lithium jet (1).

6. The apparatus according to claim 1, wherein a screening optical element (25) is placed on a laser beam axis (26) between the input window (5) and the interaction zone (2) the screening optical element (25) is heated up to 350-400° C. and consists of a chemically high-resistant material, with high resistivity to liquid Lithium at high temperatures.

7. The apparatus according to claim 6, wherein the screening optical element (25) is made of sapphire, and laser beam light wavelength is in the range of 0.3-3.5 um.

8. The apparatus according to claim 6, wherein the input window (5) and screening optical element (25) are adjoined to a sub-chamber (29) with the gas inlet (4), providing the pressure difference on both sides of the screening optical element (25).

9. The apparatus according to claim 6, wherein the screening optical element (25) is a focusing lens.

10. The apparatus according to claim 1, wherein an external side of the nozzle (10) has a ceramic lining (13) next to an outlet of the nozzle (10).

11. The apparatus according to claim 1, wherein the etendue of EUV light source output to the collector mirror is in a range of $5 \cdot 10^{-4}$ mm²·sr to $1,5 \cdot 10^{-2}$ mm²·sr.

12. The apparatus according to claim 1, wherein a laser beam axis (26) and a direction (32) of EUV-light beam output from interaction zone to the collector mirror form two angles to a normal line (31) to a lithium jet surface more than 0 degree.

13. The apparatus according to claim 1, wherein a high temperature pump (11) is either a magneto-hydrodynamic ("MHD") pump or a magnetically driven vane pump with a heatproof magnetic coupling.

14. A method for generating extreme ultraviolet ("EUV") light from a laser produced plasma ("LPP"), said method comprising:

producing a laser target as a continuous liquid Lithium jet, delivered in an interaction zone in a vacuum chamber, while liquid Lithium is pumped in a closed loop system, irradiating at high repetition rate the continuous liquid Lithium jet by a laser beam, introduced into the interaction zone through an input window of the vacuum chamber, a screening optical element and an opening in a protective shield, surrounding the continuous liquid Lithium jet, while an optical axis of the laser beam is different from a normal line to a continuous liquid Lithium jet surface, sending out EUV light from the laser-produced plasma to a collector mirror through another opening in the protective shield and a EUV spectral purity filter, configured as an EUV exit window for the vacuum chamber.

15. The method according to claim 14, wherein a temperature of the protective shield is maintained above lithium's melting point of 180° C.

16. The method according to claim 14, wherein a temperatures of the screening optical element and the EUV spectral purity filter are maintained in a range of 350 to 450° C.

17. The method according to claim 14, wherein inert gas pressures on outward sides of the EUV spectral purity filter and the screening optical element are maintained higher than a pressure inside the vacuum chamber.

* * * * *